(12) United States Patent
Lockhart

(10) Patent No.: US 7,775,994 B2
(45) Date of Patent: Aug. 17, 2010

(54) ULTRASOUND MEDICAL SYSTEMS AND RELATED METHODS

(75) Inventor: Joseph Lockhart, Chestnut Hill, MA (US)

(73) Assignee: Emigrant Bank, N.A., New York, NY (US)

(*) Notice: Subject to any disclaimer, the term of this patent is extended or adjusted under 35 U.S.C. 154(b) by 590 days.

(21) Appl. No.: 11/609,126

(22) Filed: Dec. 11, 2006

(65) Prior Publication Data

US 2008/0139971 A1    Jun. 12, 2008

(51) Int. Cl.
*A61H 1/00* (2006.01)
(52) U.S. Cl. ........................... 601/2; 600/437
(58) Field of Classification Search ............. 601/2; 600/437
See application file for complete search history.

(56) References Cited

U.S. PATENT DOCUMENTS

| | | | |
|---|---|---|---|
| 4,870,953 A | 10/1989 | DonMicheal et al. | |
| 4,920,954 A | 5/1990 | Alliger et al. | |
| 4,961,424 A | 10/1990 | Kubota et al. | |
| 5,069,664 A | 12/1991 | Guess et al. | |
| 5,324,255 A | 6/1994 | Passafaro et al. | |
| 5,334,183 A | 8/1994 | Wuchinich | |
| 5,351,693 A | 10/1994 | Taimisto et al. | |
| 5,421,336 A | 6/1995 | De Bernardis | |
| 5,524,620 A | 6/1996 | Rosenschein | |
| 5,713,848 A | 2/1998 | Dubrul et al. | |
| 5,944,687 A | 8/1999 | Benett et al. | |
| 6,039,695 A | 3/2000 | Sakamoto et al. | |
| 6,193,669 B1 | 2/2001 | Degany et al. | |
| 6,354,999 B1 | 3/2002 | Dgany et al. | |
| 6,524,251 B2 | 2/2003 | Rabiner et al. | |
| 6,551,337 B1 | 4/2003 | Rabiner et al. | |
| 6,558,334 B2 | 5/2003 | Shalman et al. | |
| 6,660,013 B2 | 12/2003 | Rabiner et al. | |
| 6,689,087 B2 | 2/2004 | Pal et al. | |
| 6,695,781 B2 | 2/2004 | Rabiner et al. | |
| 6,730,048 B1 | 5/2004 | Hare et al. | |
| 7,074,188 B2 | 7/2006 | Nair et al. | |
| 2002/0029054 A1 | 3/2002 | Rabiner et al. | |
| 2002/0107446 A1 | 8/2002 | Rabiner et al. | |
| 2003/0069590 A1 | 4/2003 | Rabiner et al. | |
| 2004/0162571 A1 | 8/2004 | Rabiner et al. | |
| 2005/0043753 A1 | 2/2005 | Rabiner et al. | |
| 2005/0096669 A1 | 5/2005 | Rabiner et al. | |
| 2005/0119679 A1 | 6/2005 | Rabiner et al. | |
| 2005/0187513 A1 | 8/2005 | Rabiner et al. | |
| 2005/0187514 A1 | 8/2005 | Rabiner et al. | |
| 2005/0273090 A1 | 12/2005 | Nieman et al. | |
| 2005/0288654 A1 | 12/2005 | Nieman et al. | |
| 2007/0085611 A1 | 4/2007 | Gerry et al. | |

FOREIGN PATENT DOCUMENTS

| | | |
|---|---|---|
| WO | WO 01/24715 | 4/2001 |
| WO | WO 01/24716 | 4/2001 |
| WO | WO 02/13678 | 2/2002 |
| WO | WO 2004/058074 | 7/2004 |

*Primary Examiner*—Long V Le
*Assistant Examiner*—Saurel J Selkin
(74) *Attorney, Agent, or Firm*—Greenberg Traurig, LLP; David J. Dykeman; Danielle T. Abramson

(57) ABSTRACT

Ultrasound medical systems and related methods are described.

30 Claims, 4 Drawing Sheets

ULTRASOUND MEDICAL SYSTEMS AND RELATED METHODS

TECHNICAL FIELD

This invention relates to ultrasound medical systems and related methods.

BACKGROUND

An ultrasound medical device can be used to treat certain medical conditions. Typically, a portion of the ultrasound medical device is disposed within a subject (e.g., a human), and then the ultrasound medical device is activated so that the portion of the ultrasound medical device disposed within the subject vibrates at an ultrasonic frequency. The ultrasonic vibrations can be used to treat the medical condition (e.g., by ablating tissue in the subject). For example, the ultrasound medical device can be used to treat an occluded region of a blood vessel in a subject by disposing a portion of the ultrasound medical device within the occluded region of the blood vessel and then vibrating the ultrasound medical device at an ultrasonic frequency to ablate the occluded region of the blood vessel.

SUMMARY

In one aspect of the invention, an ultrasound medical system includes an ultrasound probe configured to be disposed within a body vessel of a subject and to emit a therapeutic level of vibrational energy within the body vessel during use. The medical system further includes an ultrasound device adapted to extracorporeally deliver vibrational energy to the body vessel during use. The vibrational energy delivered by the ultrasound device during use is capable of interacting with the vibrational energy emitted by the ultrasound probe during use to treat the body vessel.

In another aspect of the invention, an ultrasound medical system includes an ultrasound probe configured to be disposed within a body vessel of a subject and an ultrasound device configured to be disposed outside of the subject and adapted to detect vibrational energy emitted by the ultrasound probe during use. The ultrasound probe is adapted to be controlled by vibrational energy detected by the ultrasound device.

In an additional aspect of the invention, a method includes emitting a first vibrational energy within a region of a body vessel of a subject and extracorporeally delivering a second vibrational energy to the region of the body vessel. The first and second vibrational energies are adapted to interact with one another to treat the body vessel.

In a further aspect of the invention, a method includes emitting a first vibrational energy within a body vessel of a subject, detecting vibrational energy with an ultrasound device disposed outside the subject, and extracorporeally delivering a second vibrational energy to the body vessel. The second vibrational energy is delivered based on the vibrational energy detected by the ultrasound device.

In another aspect of the invention a method includes detecting vibrational energy emitted by an ultrasound probe disposed within a body vessel of a subject using an ultrasound device disposed outside of the subject and vibrating the ultrasound probe based on the vibrational energy detected by the ultrasound device.

Embodiments may include one or more of the following features.

In some embodiments, the ultrasound device is adapted to extracorporeally deliver vibrational energy capable of interacting with the vibrational energy emitted by the ultrasound probe to treat the body vessel.

In certain embodiments, the ultrasound device is adapted to extracorporeally deliver vibrational energy having a frequency substantially equal to a frequency of vibrational energy emitted from the ultrasound probe during use.

In some embodiments, the ultrasound device is adapted to extracorporeally deliver vibrational energy having a phase substantially equal to a phase of vibrational energy emitted from the ultrasound probe during use.

In certain embodiments, the ultrasound device is configured to be disposed outside of the subject, adjacent the ultrasound probe.

In some embodiments, the ultrasound device includes an ultrasound transducer (e.g., a high-intensity focused ultrasound transducer).

In certain embodiments, the ultrasound device is configured to detect vibrational energy emitted by the ultrasound probe during use.

In some embodiments, the ultrasound probe is adapted to be controlled based on the vibrational energy detected by the ultrasound device.

In some embodiments, medical system further includes a control unit adapted to control the ultrasound probe based on vibrational energy detected by the ultrasound device (e.g., based on a difference between the vibrational energy detected by the ultrasound device and the vibrational energy emitted by the ultrasound probe).

In certain embodiments, the control unit is adapted to supply energy to the ultrasound probe based on the vibrational energy detected by the ultrasound device.

In some embodiments, the control unit is adapted to supply electrical energy to an acoustic assembly coupled with the ultrasound probe. The acoustic assembly can be adapted to convert the electrical energy into vibrational energy.

In certain embodiments, the control unit includes a processor adapted to determine a level of energy to supply to the ultrasound probe.

In some embodiments, the control unit includes a look-up table to determine a level of energy to supply to the ultrasound probe.

In certain embodiments, the control unit is in communication with the ultrasound probe and the ultrasound device.

In some embodiments, the ultrasound device is adapted to be controlled based on the vibrational energy detected by the ultrasound device.

In some embodiments, the medical system further includes a control unit adapted to control the ultrasound device based on the vibrational energy detected by the ultrasound device (e.g., based on a difference between the vibrational energy detected by the ultrasound device and the vibrational energy emitted by the ultrasound probe).

In certain embodiments, the control unit is adapted to control the vibrational energy extracorporeally delivered by the ultrasound device based on the vibrational energy detected by the ultrasound device.

In some embodiments, the ultrasound probe has a diameter of about 0.002 inch to about 0.01 inch.

In certain embodiments, the control unit is adapted to control a supply of energy to the ultrasound probe based on the vibrational energy detected by the ultrasound device.

In some embodiments, the ultrasound device is adapted to extracorporeally deliver vibrational energy to the body vessel.

In certain embodiments, the control unit is adapted to control a supply of energy to the ultrasound device based on the vibrational energy detected by the ultrasound device.

In some embodiments, the first vibrational energy has a first frequency and the second vibrational energy has a second frequency substantially equal to the first frequency.

In certain embodiments, the first vibrational energy has a first phase and the second vibrational energy has a second phase substantially equal to the first phase.

In some embodiments, emitting the first vibrational energy includes vibrating an ultrasound probe disposed within the region of the body vessel.

In certain embodiments, the second vibrational energy is extracorporeally delivered by an ultrasound device disposed outside of the subject.

In some embodiments, the second vibrational energy is extracorporeally delivered based on a difference between the vibrational energy detected by the ultrasound device and the first vibrational energy.

In certain embodiments, emitting the first vibrational energy includes vibrating an ultrasound probe disposed within the body vessel.

In some embodiments, the ultrasound probe is disposed within an occluded region of the body vessel.

In certain embodiments, the method further includes determining a property of the occluded region of the vessel based on the energy detected by the ultrasound device (e.g., based on a difference between the vibrational energy detected by the ultrasound device and the first vibrational energy).

In some embodiments, the property of the occluded region is a hardness of the occluded region.

In certain embodiments, the property of the occluded region is a density of the occluded region.

In some embodiments, the property of the occluded region is determined based on one or more characteristics of the vibrational energy detected by the ultrasound device. The one or more characteristics can be frequency, amplitude, phase, duty cycle, and/or pulse repetition frequency.

In certain embodiments, the ultrasound probe is vibrated at a frequency of about 10 KHz to about 100 KHz.

In some embodiments, the second vibrational energy is extracorporeally delivered based on one or more characteristics of the vibrational energy detected by the ultrasound device. The one or more characteristics can be frequency, amplitude, phase, duty cycle, and/or pulse repetition frequency.

In certain embodiments, emitting the first vibrational energy includes vibrating an ultrasound probe disposed within the body vessel, and the ultrasound device is disposed adjacent the ultrasound probe.

In some embodiments, the first and second vibrational energies are adapted to interact with one another to treat the body vessel.

In certain embodiments, the second vibrational energy has a frequency substantially equal to a frequency of the first vibrational energy.

In some embodiments, the second vibrational energy has a phase substantially equal to a phase of the first vibrational energy.

In certain embodiments, vibrating the ultrasound probe includes supplying energy to the ultrasound probe.

In some embodiments, the energy is supplied to the ultrasound probe based on the vibrational energy detected by the ultrasound device.

In certain embodiments, the energy is supplied to the ultrasound probe based on one or more characteristics of the vibrational energy defected by the ultrasound device. The one or more characteristics can be frequency, amplitude, phase, duty cycle, and pulse repetition frequency.

In some embodiments, the method further includes extracorporeally delivering a second vibrational energy to the body vessel.

In certain embodiments, the second vibrational energy is extracorporeally delivered by the ultrasound device.

In some embodiments, the method further includes detecting vibrational energy with an ultrasound device disposed outside of the subject.

In some embodiments, the method further includes extracorporeally delivering the second vibrational energy based on the vibrational energy detected by the ultrasound device.

In some embodiments, the method further includes emitting the first vibrational energy based on the vibrational energy detected by the ultrasound device.

Embodiments may include one or more of the following advantages.

In some embodiments, vibrational energy (e.g., ultrasonic energy) is extracorporeally delivered to a body vessel (e.g., by activating an ultrasound transducer disposed outside of the subject) while emitting vibrational energy (e.g., ultrasonic energy) within the body vessel using an ultrasound probe disposed within the body vessel. This technique can help to increase the total amount of vibrational energy that can be delivered to the body vessel without substantially altering the physical properties of the ultrasound probe due to the increased vibrational energy.

In certain embodiments, the methods can be used to treat regions (e.g., occluded regions) of relatively small body vessels (e.g., neuro blood vessels, neuro internal carotid vessels, brachial vessels, coronary circumflex vessels, anterior tibial vessels, etc.). The treatment of relatively small blood vessels can involve the use of a relatively small or fine ultrasound probe disposed within the vessel. By extracorporeally delivering vibrational energy (e.g., ultrasonic energy) to the vessel in addition to activating the relatively small or fine ultrasound probe disposed within the vessel, a sufficient amount of vibrational energy can be delivered to the vessel to treat the vessel without substantially altering the physical properties of the ultrasound probe.

In some embodiments, the methods can be used to treat regions (e.g., occluded regions) of relatively large body vessels (e.g., iliac vessels, subclavian vessels, femoral vessels, aortas, vena cavas, etc.). Such relatively large body vessels sometimes require substantially increased levels of vibrational energy (e.g., ultrasonic energy) to be delivered to the body vessel during treatment. Due to these increased levels of vibrational energy, traditional methods of treating such body vessels can require the use of an ultrasound probe with a substantially increased diameter, and thus a substantially increased stiffness. By extracorporeally delivering vibrational energy to the vessel in addition to activating an ultrasound probe disposed within the vessel, a sufficient amount of vibrational energy can be delivered to the vessel to treat the vessel without having to substantially increase the size of the ultrasound probe. As a result, ultrasound probes having sufficient flexibility to be navigated through the vessel can be used to treat the relatively large vessel.

In certain embodiments, an ultrasound device (e.g., an ultrasound transducer) disposed outside of the subject is used to detect vibrational energy (e.g., ultrasonic energy) emitted by an ultrasound device (e.g., an ultrasound probe) disposed within a body vessel of the subject. The ultrasound device disposed within the body vessel can be operated based on the vibrational energy detected by the ultrasound device disposed outside of the subject. As a result, the operation of the ultrasound device disposed within the body vessel can be tailored to one or more properties of the body vessel. This can help to ensure that sufficient energy levels are generated by the ultrasound device disposed within the body vessel and can help to prevent the generation of excessive amounts of vibrational energy by the ultrasound device. As a result, treatment time can be reduced and the alteration of healthy body vessel tissue (e.g., by delivering excessive amounts of vibrational energy to the body vessel) can be reduced or prevented.

Other aspects, features, and advantages are in the description, the drawings, and the claims.

DETAILED DESCRIPTION

This disclosure relates to ultrasound medical systems and related methods. Some of the methods include emitting vibrational energy (e.g., ultrasonic energy) within a targeted region (e.g., an occluded region) of a body vessel (e.g., a blood vessel) of a subject and extracorporeally delivering vibrational energy (e.g., ultrasonic energy) to the targeted region of the body vessel. The extracorporeally delivered vibrational energy can serve to supplement the vibrational energy emitted within the vessel, or vice versa. Certain methods include activating a first ultrasound device (e.g., an ultrasound probe) disposed within the targeted region of the body vessel, and detecting vibrational energy emitted from the first ultrasound device using a second ultrasound device (e.g., an ultrasound transducer) that is disposed outside of the subject. The first ultrasound device can be controlled based on the vibrational energy detected by the second ultrasound device to treat the targeted region of the body vessel. In some embodiments, the second ultrasound device, which is disposed outside of the subject, is adapted to extracorporeally deliver vibrational energy (e.g., ultrasonic energy) to the targeted region of the vessel. The vibrational energy that is extracorporeally delivered to the targeted region by the second ultrasound device can be controlled based on the vibrational energy that it detects.

Figure 1:
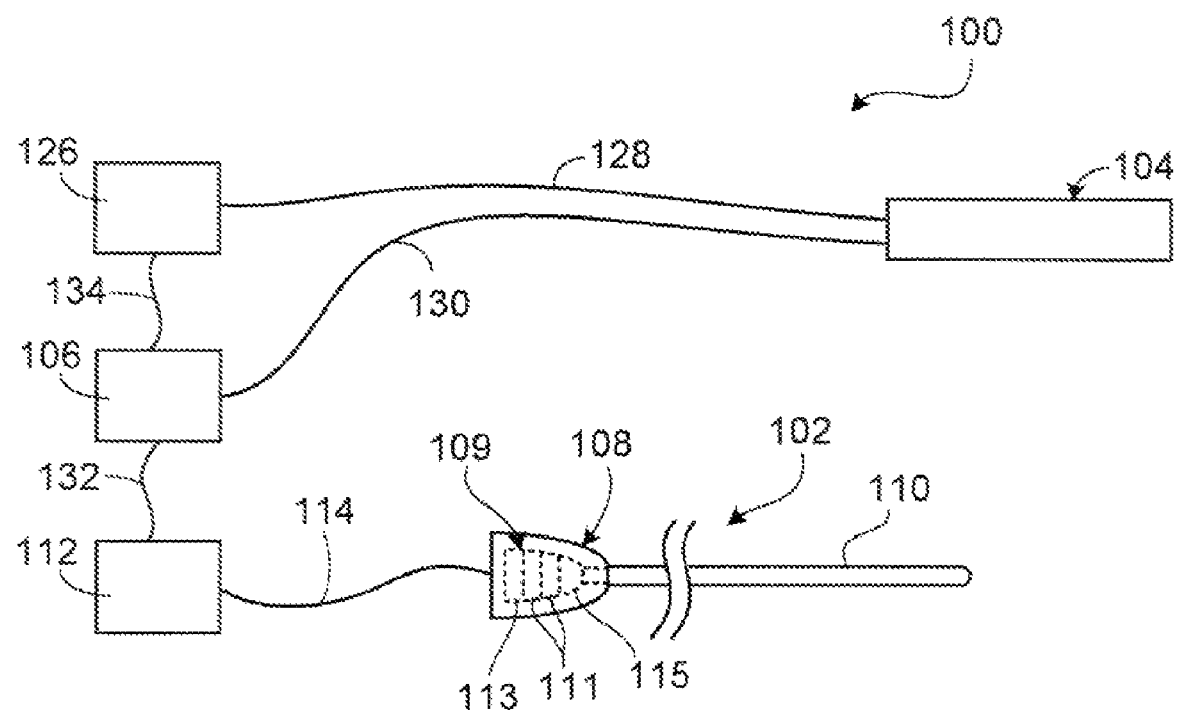
FIG. 1 is a schematic of an ultrasound medical system.

FIG. 1 is a schematic of an ultrasound medical system 100 that includes an ultrasound medical device 102, an ultrasound transducer 104, and a control unit 106. Ultrasound medical device 102 includes a hand piece assembly 108 and an ultrasound wire or probe 110. An acoustic horn assembly 109 is disposed within hand piece assembly 108. Acoustic horn assembly 109 includes piezoelectric elements 111 disposed between a back mass 113 and a transducer horn 115. A power supply 112 is in electrical communication with piezoelectric elements 111 of acoustic horn assembly 109. Power supply 112 can, for example, be electrically connected to piezoelectric elements 111 by a wire 114. Transducer horn 115 of acoustic horn assembly 109 is coupled (e.g., mechanically coupled) with ultrasound probe 110. Ultrasound medical device 102 is configured so that when power supply 112 provides electrical energy (e.g., an oscillating voltage) to acoustic horn assembly 109 (e.g., to piezoelectric elements 111 of acoustic horn assembly 109), acoustic horn assembly 109 converts the electrical energy to mechanical energy in the form of ultrasonic vibrations in ultrasound probe 110. Piezoelectric elements 111 can, for example, vibrate transducer horn 115 upon receiving electrical energy from power supply 112. Because transducer horn 115 is coupled to ultrasound probe 110, vibrational energy is transferred from transducer horn 115 to ultrasound probe 110, causing ultrasound probe 110 to vibrate. Examples of similar ultrasound medical devices are described in U.S. patent application Ser. No. 11/515,545, filed Sep. 5, 2006 and entitled "Ultrasound Medical Devices, Systems and Methods," which is incorporated by reference herein.

Ultrasound probe 110 is configured to vibrate transversely relative to its longitudinal axis when electrical energy is applied to acoustic horn assembly 109 of hand piece assembly 108. Examples of ultrasound probes configured to vibrate transversely are described in U.S. Pat. No. 6,551,337, which is incorporated by reference herein. Ultrasound probe 110 can have a diameter of about 0.002 inch to about 0.020 inch. In embodiments in which ultrasound probe 110 is intended to treat relatively small blood vessels (e.g., neuro vessels), the active region of ultrasound probe 110 can have a diameter of about 0.002 inch to about 0.010 inch (e.g., about 0.002 inch to about 0.005 inch). In embodiments in which ultrasound probe 110 is intended to treat relatively large blood vessels (e.g., iliac vessels), the active region of ultrasound probe 110 can have a diameter of about 0.008 inch to about 0.020 inch (e.g., about 0.015 inch to about 0.020 inch). Ultrasound probe 110 can include (e.g., can be formed of) one or more materials having physical properties to withstand the vibrational energy transmitted therethrough. In some embodiments, ultrasound probe 110 is an annealed Ti-6Al-4V titanium probe. Alternatively or additionally, ultrasound probe 110 can include one or more different materials. Examples of materials from which ultrasound probe 110 can be made include metals (e.g., titanium, stainless steel) and alloys (e.g., titanium alloys other than annealed Ti-6Al-4V titanium, stainless steel alloys).

Figure 2:
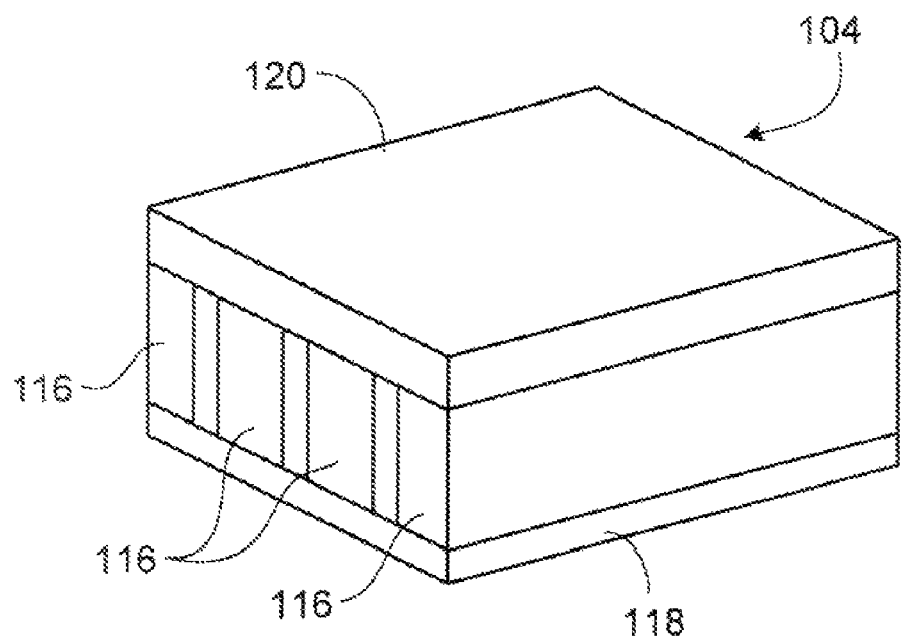
FIG. 2 is a perspective, partial cut-away view of an ultrasound transducer of the ultrasound medical system of FIG. 1.

FIG. 2 illustrates a more detailed view of ultrasound transducer 104. Referring to both FIGS. 1 and 2, ultrasound transducer 104 includes an array of piezoelectric (e.g., piezoceramic) elements 116, a matching layer 118 disposed on one side of piezoelectric elements 116, and a backing layer 120 disposed on an opposite side of piezoelectric elements 116. In some embodiments, matching layer 118 includes (e.g., is formed of) an epoxy (e.g., a composite of alumina in an epoxy matrix). Matching layer 118 can alternatively or additionally include one or more other materials. For example, matching layer 118 can include one or more polymeric materials, such as silicone, polyvinyl fluoride, etc. Matching layer 118 can enhance (e.g., optimize) the transmission of ultrasound energy into the patient by providing a medium that is intermediate in acoustic properties to that of piezoelectric elements 116 and the tissue of the patient. Backing layer 120 can include (e.g., be formed of) one or more acoustically absorptive materials. For example, backing layer 120 can include an epoxy with particles embedded therein (e.g., an flexible polymer with oxide particles embedded therein). Backing layer 120 can absorb the backward directed ultrasound energy and can reduce (e.g., eliminate) any echoes that could potentially return to transducer 104. Backing layer 120 can also serve as a damping device to restrict the time of vibration and keep the ultrasound pulse short (e.g., to preserve axial resolution). Ultrasound transducer 104, as shown in FIG. 1, is electrically connected to a power supply 126 via an electrical wire 128. Wire 128 can, for example, be connected to electrodes that are secured to piezoelectric elements 116 of ultrasound transducer 104. Ultrasound transducer 104 is also in communication with control unit 106 via a cable 130.

Ultrasound transducer 104 can be used to both emit vibrational energy and to detect vibrational energy. To emit vibrational energy from ultrasound transducer 104, electrical energy (e.g., an oscillating voltage) is delivered to ultrasound transducer 104 by power supply 126. Upon receiving the electrical energy, piezoelectric elements 116 of ultrasound transducer 104 vibrate and thus emit vibrational energy through matching layer 118. To detect vibrational energy, the delivery of electrical energy from power supply 126 to ultrasound transducer 104 is paused. During this pause, piezoelectric elements 116 can receive vibrational energy (e.g., sound waves) from another source (e.g., from ultrasound medical device 102). Upon receiving the vibrational energy, piezoelectric elements 116 can convert the vibrational energy into electrical energy, which can be transmitted to control unit 106 via cable 130. Control unit 106 can then determine a level and pattern of the vibrational energy detected by piezoelectric elements 116 based on the level and pattern of electrical energy (e.g., electrical data signals) provided to control unit 106.

In addition to being in communication with ultrasound transducer 104, control unit 106 is in communication with power supplies 112 and 126 via cables 132 and 134, respectively. Power supplies 112 and 126 can be any of various devices capable of providing electrical energy to ultrasound medical device 102 and ultrasound transducer 104, respectively. Examples of such devices include electrical generators, batteries, linear power supplies, switching power supplies. Control unit 106 can be any of various devices capable of processing electrical energy received from ultrasound transducer 104 and controlling power supplies 112 and 126 based on the electrical energy received from ultrasound transducer 104. Examples of such devices include microprocessors, Application-Specific Integrated Circuits (ASICs), and digital signal processors (DSPs). During use, as discussed below, control unit 106 can control the supply of energy from power supplies 112, 126 to ultrasound medical device 102 and ultrasound transducer 104, respectively, based on the electrical data signals received from ultrasound transducer 104. Thus, control unit 106 can control the vibrational energy emitted from ultrasound probe 110 and ultrasound transducer 104 based on the electrical data signals received from ultrasound transducer 104.

Figure 3A:
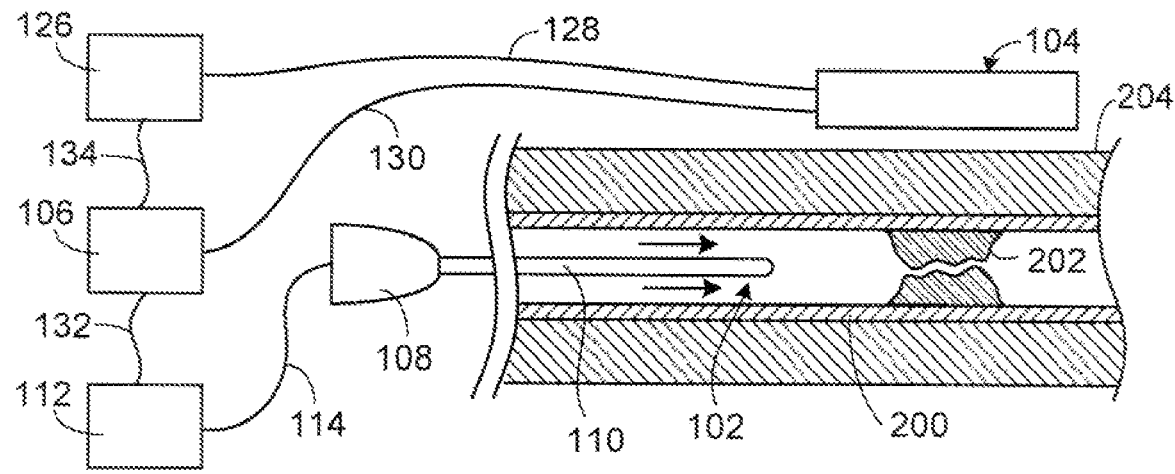
FIGS. 3A-3D illustrate a method of using the ultrasound medical system of FIG. 1.

FIGS. 3A-3D illustrate a method of using ultrasound medical system 100. Referring to FIG. 3A, during use, a distal portion of ultrasound probe 110 of ultrasound medical device 102 is inserted into a blood vessel 200 of a subject and navigated through blood vessel 200 until reaching an occluded region (e.g., a thrombus) 202 of blood vessel 200. An active region of ultrasound probe 110 (e.g., a region of ultrasound probe 110 that is configured to vibrate transversely during use) is positioned at least partially within occluded region 202 of blood vessel 200. The active region of ultrasound probe 110 can, for example, be substantially surrounded by occluded region 202.

Figure 3B:
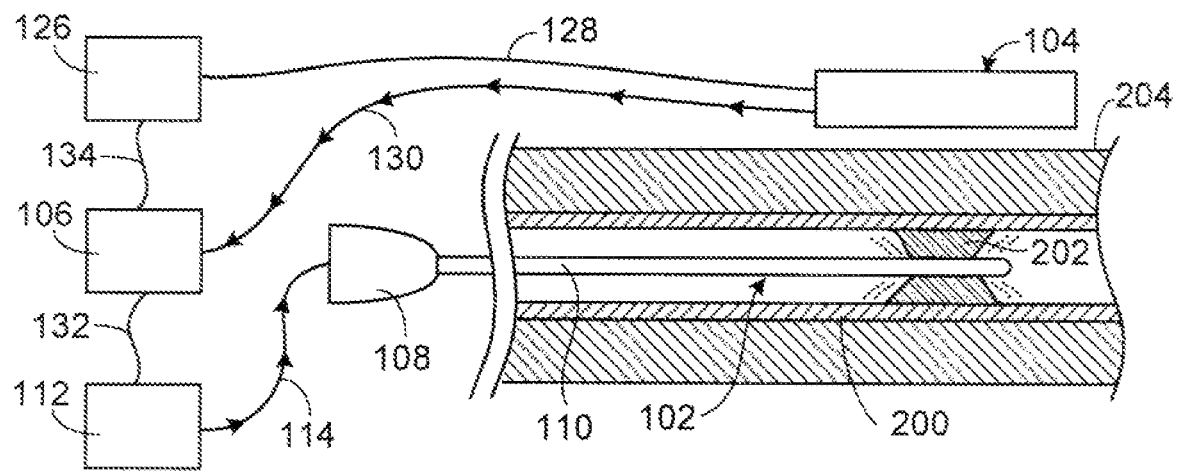

Referring to FIG. 3B, after positioning the active region of ultrasound probe 110 within occluded region 202 of blood vessel 200, ultrasound transducer 104 is disposed outside of the subject, adjacent both occluded region 202 and the active region of ultrasound probe 110. Ultrasound transducer 104 can, for example, be disposed on an outer surface 204 of the subject's skin. To dispose ultrasound transducer 104 adjacent occluded region 202, the user first determines the location of occluded region 202. The location of occluded region 202 can, for example, be determined by performing flow detection ultrasound techniques (e.g., using a CT imaging system). Any of various other techniques can alternatively or additionally be used to determine the location of occluded region 202. After determining the location of occluded region 202, ultrasound transducer 104 is fixed adjacent occluded region 202. Ultrasound transducer 104 can, for example, be held by the user adjacent occluded region 202. Alternatively or additionally, ultrasound transducer 104 can be secured to the body of the subject being treated, adjacent occluded region 202. For example, ultrasound transducer 104 can be fixed to a strap (e.g., a belt), which can be wrapped around and secured to the subject, such that ultrasound transducer 104 remains fixed adjacent occluded region 202 during the procedure. As another example, ultrasound transducer 104 can be adhesively attached to the subject adjacent occluded region 202 to secure ultrasound transducer 104 in the desired position.

After positioning ultrasound probe 110 and ultrasound transducer 104 as desired, ultrasound probe 110 is activated for a period of time to help determine certain properties of occluded region 202, which can help to determine the amount of vibrational energy required to effectively treat occluded region 202. To activate ultrasound probe 110, electrical energy is supplied to acoustic assembly 109 of hand piece 108, causing the active region of ultrasound probe 110 to vibrate in a transverse direction. In order to determine the properties of occluded region 202, ultrasound probe 110 is vibrated at a predetermined frequency, a predetermined amplitude, a predetermined duty cycle, and/or a predetermined pulse repetition frequency. In some embodiments, for example, ultrasound probe 110 is vibrated at a frequency of about 20 KHz to about 100 KHz. In certain embodiments, the active region of ultrasound probe 110 is vibrated at an amplitude of transverse displacement of about zero micrometer to about 500 micrometers (e.g., about 10 to about 200 micrometers, about 30 to about 125 micrometers). In some embodiments, ultrasound probe 110 is vibrated with a duty cycle of about 0.5 percent to about 100 percent. In certain embodiments, ultrasound probe 110 is vibrated at a pulse repetition frequency of about one Hz to about 1000 Hz.

In some embodiments, ultrasound probe 110 is vibrated for about one millisecond to about one minute (e.g., about one millisecond to about one second) to determine the properties of occluded region 202. In certain embodiments, ultrasound probe 110 is vibrated for a relatively short period of time. Ultrasound probe 110 can, for example, be vibrated for about five minutes or less (e.g., about three minutes or less, about one minute or less, about 30 seconds or less).

During the phase in which the properties of occluded region 202 are being determined, ultrasound transducer 104, which is disposed outside of the subject, is operated to detect vibrational energy (e.g., sound signals) emitted by ultrasound probe 110. For example, during this phase, substantially no electrical energy is supplied to ultrasound transducer 104 from power supply 126, allowing ultrasound transducer 104 to detect vibrational energy from ultrasound probe 110 and to transfer data signals including information related to the detected vibrational energy to control unit 106. Certain characteristics (e.g., frequency, amplitude, phase, duty cycle, pulse repetition frequency) of the vibrational energy detected by ultrasound transducer 104 will generally differ from corresponding characteristics of the vibrational energy initially emitted by ultrasound probe 110 (e.g., the vibrational energy emitted by ultrasound probe 110 prior to passing through occluded region 202 and other body matter, such as muscle, bone, and skin on route to ultrasound transducer 104). The vibrational energy emitted by ultrasound probe 110 will, for example, generally be attenuated by occluded region 202 of blood vessel 200 and other biological matter prior to being detected by ultrasound transducer 104. The degree to which the vibrational energy is attenuated prior to reaching ultrasound transducer 104 can depend on various properties (e.g., size, hardness, density, etc.) of occluded region 202. Therefore, without wishing to be bound by theory, it is believed that the change in the vibrational energy (e.g., the change in one or more characteristics of the vibrational energy) detected by ultrasound transducer 104 relative to the vibrational energy (e.g., relative to one or more corresponding characteristics of the vibrational energy) initially emitted by ultrasound probe 110 can be used to determine certain properties of occluded region 202. It is further believed that levels and patterns of energy with which to vibrate ultrasound probe 110 to effectively treat occluded region 202 can be determined based on the properties of occluded region 202. Thus, if is believed that occluded region 202 can be effectively and efficiently treated based on the difference between the vibrational energy (e.g., one or more characteristics of the vibrational energy) detected by ultrasound transducer 104 and the vibrational energy (e.g., one or more corresponding characteristics of the vibrational energy) initially emitted by ultrasound probe 110.

After detecting the vibrational energy emitted by ultrasound probe 110, ultrasound transducer 104 transmits electrical data signals related to the detected vibrational energy to control unit 106. The data signals transmitted from ultrasound transducer 104 to control unit 106 can include information regarding one or more characteristics (e.g., frequency, amplitude, phase, duty cycle, and/or pulse repetition frequency) of the vibrational energy detected by ultrasound transducer 104. Upon receiving the data signals, control unit 106 compares the characteristic(s) of the vibrational energy detected by ultrasound transducer 104 to the corresponding characteristic (s) of the vibrational energy initially emitted by ultrasound probe 110. In some embodiments, the characteristics of the vibrational energy initially emitted by ultrasound probe 110 is theoretically determined. For example, these characteristics can be determined as a function of the electrical energy supplied to acoustic horn assembly 109 of ultrasound medical device 102 and the configurations of acoustic horn assembly 109 and ultrasound probe 110. In some embodiments, for example, the vibrational energy emitted by ultrasound probe 110 has a linear relationship with the electrical energy provided to acoustic horn assembly 109. By determining the characteristic(s) of the vibrational energy initially emitted by ultrasound probe 110 and comparing that/those characteristic (s) to corresponding characteristics) of the vibrational energy detected by ultrasound transducer 104, control unit 106 can determine the extent to which the vibrational energy emitted by probe 110 was attenuated or otherwise altered while passing through occluded region 202 and other biological matter between ultrasound probe 110 and ultrasound transducer 104.

Based on the detected changes in the vibrational energy, control unit 106 can determine certain properties of occluded region 202. Consequently, control unit 106 can determine a desirable level and pattern of vibrational energy to be delivered to occluded region 202 in order to effectively treat occluded region 202 and can, therefore, determine parameters of electrical energy to be supplied to ultrasound medical device 102 and ultrasound transducer 104 to effectively treat occluded region 202. In some embodiments, for example, control unit 106 compares one or more characteristics (e.g., frequency, amplitude, phase, duty cycle, pulse repetition frequency) of the vibrational energy detected by ultrasound transducer 104 to the corresponding characteristic(s) of the vibrational energy initially emitted by ultrasound probe 110 to determine desired parameters of electrical energy to be delivered to ultrasound medical device 102 and ultrasound transducer 104 to treat occluded region 202 of blood vessel 200. Examples of parameters of electrical energy that can be controlled by control unit 106 include current, voltage, frequency, amplitude, pulse repetition frequency, and duty cycle.

Any of various processes can take place within control unit 106 to determine the appropriate parameters of electrical energy to apply to ultrasound medical device 102 and ultrasound transducer 104 to treat occluded region 202. In some embodiments, for example, control unit 106 includes a look-up table including: (1) data related to vibrational energy detected by an ultrasound transducer disposed outside of the subject; (2) data related to initial vibrational energy emitted within a blood vessel; and (3) data related to electrical energy to be supplied to ultrasound medical device 102 and ultrasound transducer 104. The data included in the look-up table can, for example, be experimental data that is compiled by emitting vibrational energy within various different types of occluded body vessel regions or occluded regions of artificial members and detecting the vibrational energy using an ultrasound transducer disposed outside of the subject. Experimentation can be performed to determine appropriate amounts of vibrational energy to be supplied to the occluded region to effectively treat the occluded region. Similarly, experimentation can be performed to determine appropriate levels of electrical energy (e.g., parameters of electrical energy) to be provided to the ultrasound probe while disposed within the occluded region of the vessel and to the ultrasound transducer while disposed outside of the subject to generate the desired amounts of vibrational energy to treat the occluded region. The resulting data can be saved within the look-up table in control unit 106. Therefore, control unit 106 can determine desirable levels of electrical energy (e.g., parameters of electrical energy) to be supplied to ultrasound medical device 102 and ultrasound transducer 104 by matching the data related to the vibrational energy detected by ultrasound transducer 104 and the vibrational energy initially emitted by ultrasound probe 110 to the corresponding data related to the electrical energy to be delivered to ultrasound medical device 102 and ultrasound transducer 104.

Figure 3C:
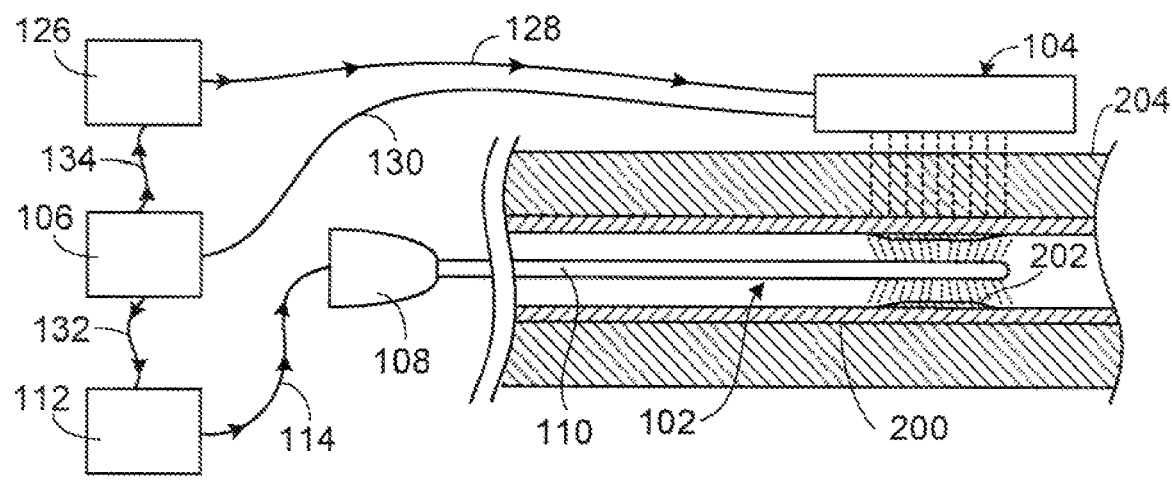
Figure 3D:
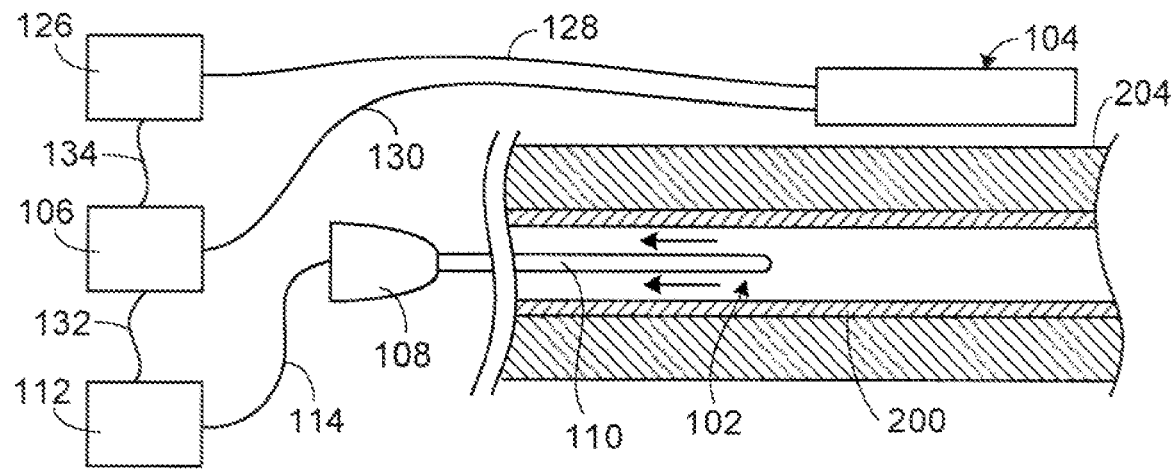

Referring to FIG. 3C, after determining the desired electrical energy (e.g., parameters of electrical energy) to be delivered to ultrasound medical device 102 and ultrasound transducer 104, control unit 106 transmits signals to power supplies 112, 126, causing power supplies 112, 126 to deliver electrical energy having the desired parameters to ultrasound medical device 102 and ultrasound transducer 104, respectively. Control unit 106 can help to ensure that effective amounts of vibrational energy are delivered to occluded region 202 and can help to prevent excessive amounts of vibrational energy from being delivered to occluded region 202. As a result, the efficiency of the treatment can be increased or maximized. For example, the treatment time and the amount of vibrational energy used during the treatment can be reduced or minimized, as discussed below.

Upon receiving electrical energy from their respective power supplies 112, 126, ultrasound medical device 102 (e.g., ultrasound probe 110 of ultrasound medical device 102) and ultrasound transducer 104 emit vibrational energy having desired parameters (e.g., desired frequency, amplitude, duty cycle, and/or pulse repetition frequency) to effectively treat occluded region 202 of blood vessel 200. In some embodiments, as shown in FIG. 3C, vibrational energy is delivered to occluded region 202 using both ultrasound transducer 104 and ultrasound probe 110. In such embodiments, the vibrational energy delivered by the ultrasound transducer 104 can interact with the vibrational energy delivered by ultrasound probe 110 to enhance or improve treatment of occluded region 202. Ultrasound transducer 104 and ultrasound probe 110 can, for example, be controlled to provide vibrational energy having substantially the same frequency and substantially the same phase at the target site (e.g., at occluded region 202). Ultrasound transducer 104 can be operated to account for energy losses that occur when passing through biological matter between ultrasound transducer 104 and occluded region 202. Ultrasound transducer 104 can, for example, be operated to emit vibrational energy having a higher frequency and/or a different phase than vibrational energy entitled by ultrasound probe 110 so that, after incurring losses as a result of passing through the biological matter between ultrasound transducer 104 and occluded region 202, the energies emitted by ultrasound transducer 104 and ultrasound probe 110 have substantially the same frequency and/or phase.

Figure 4:
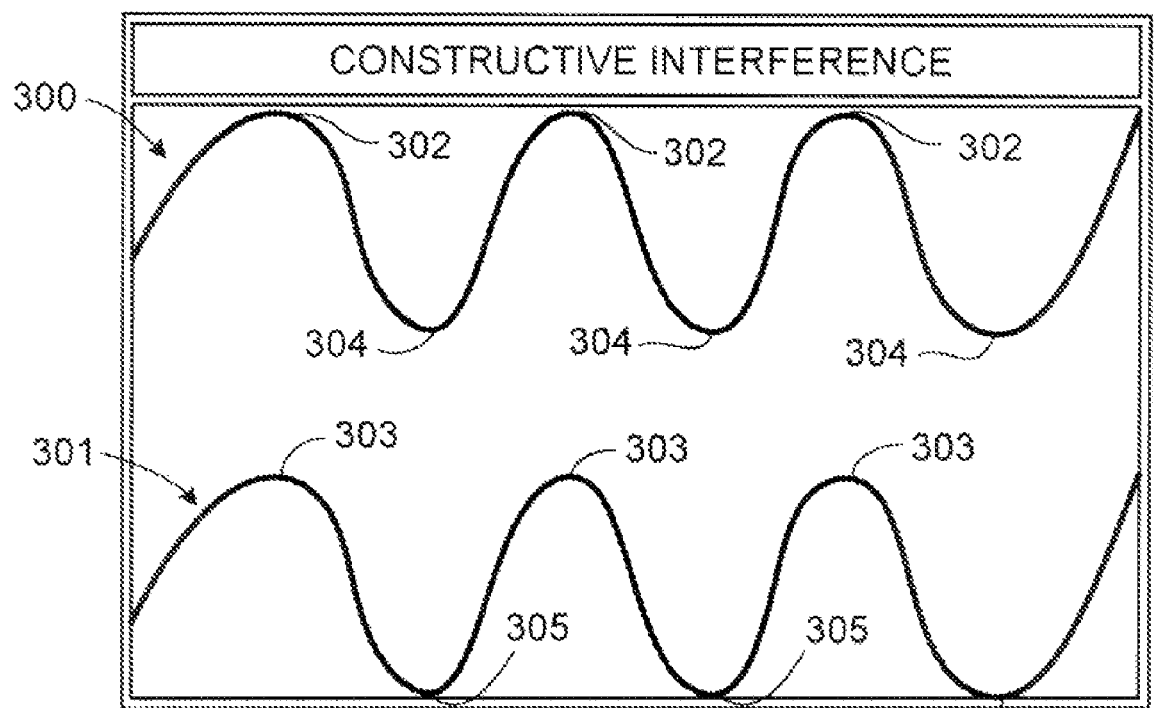
FIG. 4 is a graph displaying two vibrational waves adapted to produce constructive interference.

Referring briefly to FIG. 4, when two vibrational energy waves 300, 301 having the same wavelength are delivered in phase, crests 302, 303 of the respective energy waves coincide with one another and troughs 304, 305 of the respective energy waves coincide with one another such that the amplitude of the resultant wave has twice the amplitude of the amplitude of individual waves 300 and 301. This is commonly referred to as constructive interference. In certain embodiments, during use of ultrasound medical system 100, the vibrational energy delivered to occluded region 202 by ultrasound transducer 104 and the vibrational energy delivered to occluded region 202 by ultrasound probe 110 are maintained in substantially the same phase, resulting in constructive interference at occluded region 202. Thus, the vibrational energy that is extracorporeally delivered to occluded region 202 by ultrasound transducer 104 supplements the vibrational energy delivered to occluded region 202 by ultrasound probe 110. As a result, the total amount of vibrational energy delivered to occluded region 202 can exceed the amount of vibrational energy that ultrasound probe 110 alone is capable of emitting. Consequently, occluded regions that could not be effectively treated using only an ultrasound probe can be effectively treated using certain methods described herein.

Figure 5:
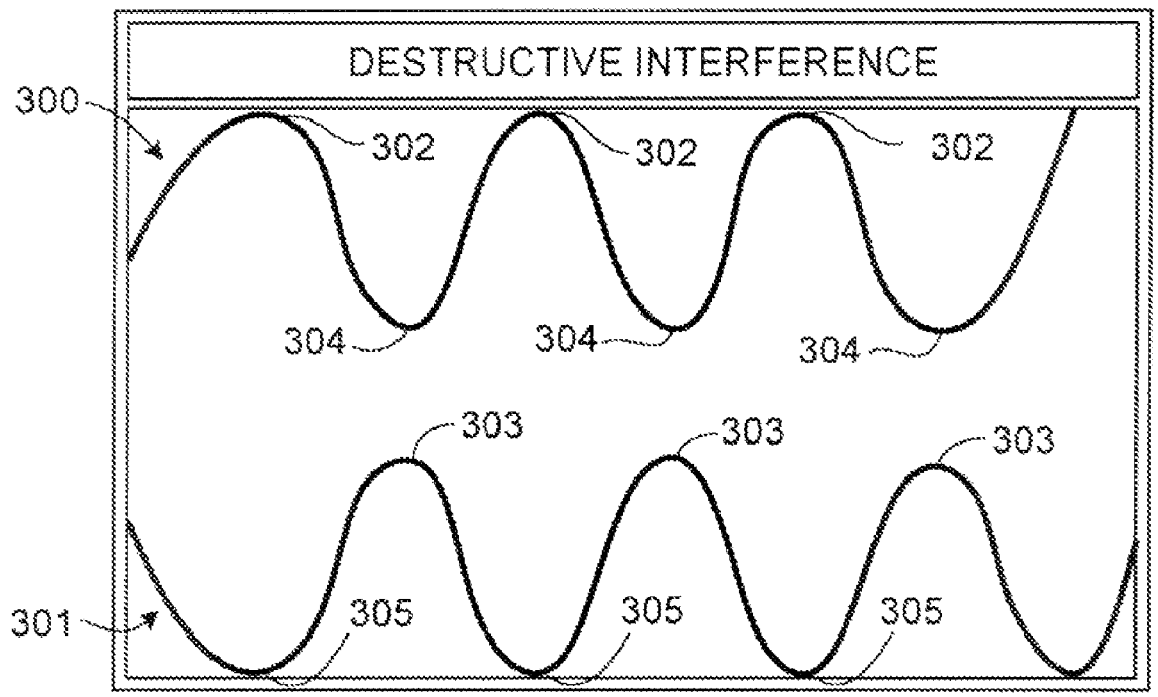
FIG. 5 is a graph displaying two vibrational waves adapted to produce constructive interference.

In some embodiments, it can be beneficial to maintain the vibrational energies delivered by ultrasound transducer 104 and ultrasound probe 110 substantially out of phase. Referring briefly to FIG. 5, when two vibrational energy waves 300, 301 having the same wavelength are delivered completely out of phase, crests 302 of energy wave 300 coincide with troughs 305 of energy wave 301 and troughs 304 of energy wave 300 coincide with crests 303 of energy wave 301 such that the two waves substantially cancel each other out. This is commonly known as destructive interference. During use of ultrasound medical system 100, the vibrational energy delivered by ultrasound transducer 104 and ultrasound probe 110 cart be controlled such that destructive interference occurs in one or more regions where ultrasound treatment is not desired (e.g., in one or more regions including healthy tissue). As a result, alteration of certain regions of healthy tissue can be reduced or prevented.

While embodiments above describe using both ultrasound probe 110 and ultrasound transducer 104 to deliver vibrational energy to occluded region 202, in some embodiments, only ultrasound probe 110 is used to deliver vibrational energy to occluded region 202. Ultrasound probe 110 can, for example, be used by itself when relatively low levels of vibrational energy are required to effectively treat occluded region 202.

Control unit 106 can be used to determine whether to use one or both of ultrasound probe 110 and ultrasound transducer 104 to deliver vibrational energy to occluded region 202 based on the energy detected by ultrasound transducer 104. For example, if, based on the energy detected fry ultrasound transducer 104, control unit 106 determines that the total amount of vibrational energy desired to treat occluded region 202 falls within a range that ultrasound probe 110 is capable of generating (e.g., capable of generating without substantial risk of damage to ultrasound probe 110), then control unit 106 can cause only ultrasound probe 110 to be vibrated to treat occluded region 202. However, if control unit 106 determines that the amount of vibrational energy desired to treat occluded region 202 exceeds an amount that ultrasound probe 110 is capable of delivering (e.g., exceeds an amount that ultrasound probe 110 is capable of delivering without substantial risk of damage to ultrasound probe 110), control unit 106 can cause both ultrasound probe 110 and ultrasound transducer 104 to deliver vibrational energy to occluded region 202, as illustrated in FIG. 3C.

In some embodiments, during treatment of occluded region 202, ultrasound transducer 104 periodically (e.g., about every 100 microseconds to about every 10 seconds) detects vibrational energy emitted by ultrasound probe 110 and, in accordance with the discussion above, ultrasound transducer 104 transmits data signals related to the detected energy to control unit 106. As a result, the parameters of the electrical energy delivered to ultrasound medical device 102 (e.g., acoustic horn assembly 109 of ultrasound medical device 102) and ultrasound transducer 104 can be altered periodically in response to changes in certain properties of occluded region 202 during treatment. This can be advantageous because the levels of vibrational energy desired to effectively treat occluded region 202 can change throughout the treatment. For example, as ultrasound probe 110 is vibrated, occluded region 202 of blood vessel 200 is ablated, and the ablation of occluded region 202 can alter the operating parameters of ultrasound probe 110 that most efficiently treat occluded region 202. Therefore, periodically altering the parameters of the electrical energy that is delivered to ultrasound medical device 102 and ultrasound transducer 104 can help to ensure that the vibrational energy delivered to occluded region 202 is maintained at a level capable of ablating occluded region 202 while helping to prevent excessive amounts of vibrational energy from being delivered to occluded region 202. As a result, the effectiveness and efficiency of the treatment can be increased or maximized.

As an alternative to detecting the vibrational energy periodically, the vibrational energy can be detected substantially continuously. Similarly, the parameters of the energy supplied to ultrasound medical device 102 and ultrasound transducer 104 can be updated substantially continuously.

During treatment, ultrasound probe 110 and ultrasound transducer 104 can be vibrated in a manner to effectively treat occluded region 202. In some embodiments, for example, ultrasound probe 110 is vibrated in a manner to generate vibrational energy having a frequency of about 20 KHz to about 100 KHz, an amplitude of about zero micrometer to about 500 micrometers (e.g., about ten micrometers to about 200 micrometers, about 30 micrometers to about 125 micrometers), a duty cycle of about 0.5 percent to about 100 percent, and/or a pulse repetition frequency of about one Hz to about 1000 Hz. In some embodiments, ultrasound transducer 104 is vibrated in a manner to generate vibrational energy having a frequency of about 20 KHz to about ten MHz, an amplitude of about zero W/cm$^2$ to about 1000 W/cm$^2$ (e.g., about three W/cm$^2$ to about 100 W/cm$^2$), a duty cycle of about 0.5 percent to about 100 percent, and/or a pulse repetition frequency of about one Hz to about ten KHz.

Vibrational energy can continue to be applied to occluded region 202 of blood vessel 200 until occluded region 202 has been substantially removed from blood vessel 200. In some embodiments, control unit 106, based on the energy detected by ultrasound transducer 104, can determine whether the treatment is complete (e.g., whether occluded region 202 has been substantially removed from blood vessel 200). For example, characteristics of vibrational energy received by ultrasound transducer 104 can be compared to corresponding data in a look-up table to determine whether occluded region 202 has been substantially removed. Alternatively or additionally, measurements of the flow rate within region 202 and/or the amount of time elapsed since the start of treatment can be used to determine when treatment is complete.

Referring to FIG. 2D, after completing treatment of occluded region 202, ultrasound probe 110 is removed from blood vessel 200. Ultrasound transducer 104 can similarly be removed from its position outside the subject and adjacent occluded region 202 of blood vessel 200.

While certain embodiments were described above, other embodiments are possible.

As an example, while ultrasound medical device 102 has been described as including acoustic assembly 109 with piezoelectric elements 111 to vibrate ultrasound probe 110, one or more other devices or assemblies can alternatively or additionally be used to vibrate ultrasound probe 110. For example, piezoelectric transducers, magnetostrictive transducers, pneumatic transducers, and/or hydraulic transducers can be used to vibrate ultrasound probe 110.

As another example, while ultrasound probe 110 has been described as being configured to vibrate transversely in embodiments above, ultrasound probe 110 can alternatively or additionally be configured to vibrate in other ways. In certain embodiments, for example, ultrasound probe 110 is configured to vibrate in a torsional direction relative to the longitudinal axis of the probe. Ultrasound probes configured to vibrate torsionally are described, for example, in U.S. Published Patent Application Nos. 2005/0187514 and 2005/0187513, which are incorporated by reference herein. Alternatively or additionally, ultrasound probe 110 can be configured to vibrate in a longitudinal direction.

As a further example, while ultrasound medical device 102 has been described as including ultrasound probe 110, ultrasound medical device 102 can alternatively or additionally include one or more other devices capable of being disposed within a body vessel and producing vibrational energy (e.g., ultrasonic energy). In certain embodiments, for example, ultrasound medical device 102 includes an RF transmitter.

As another example, in certain embodiments, ultrasound transducer is a HIFU (high-intensity focused ultrasound) transducer.

As an additional example, while ultrasound medical system 100 has been described as including two separate power supplies for ultrasound medical device 102 and ultrasound transducer 104, respectively, ultrasound medical system 100 can alternatively include a single power supply arranged to supply power to both ultrasound medical device 102 and ultrasound transducer 104.

As a further example, while methods described above include using both ultrasound medical device 102 and ultrasound transducer 104 to treat occluded region 202 or using only ultrasound medical device 102 to treat occluded region 202, other techniques can be used. In some embodiments, for example, ultrasound transducer 104 alone can be used to deliver vibrational energy to occluded region 202 during treatment. Ultrasound transducer 104 can, for example, be used when relatively small amounts of vibrational energy are desired to treat occluded region 202. Control unit 106 can be used to determine whether it is appropriate to use ultrasound transducer 104 alone by using any of the various techniques described herein. Ultrasound transducer 104 can similarly be used, without the accompanied use of ultrasound probe 110, to assess one or more properties of occluded region 202. For example, ultrasound transducer 104 can be used to detect the rate of flow through occluded region 202 prior to treatment.

As another example, while the methods described above include disposing ultrasound transducer 104 adjacent occluded region 202 of blood vessel 200 after disposing ultrasound probe 110 within occluded region 202, ultrasound transducer 104 can alternatively be disposed adjacent occluded region 202 of blood vessel 200 prior to disposing ultrasound probe 110 within occluded region 202.

As a further example, while control unit 106 has been described as being used to determine and deliver electrical energy having desirable parameters to ultrasound medical device 102, control unit 106 can alternatively or additionally be used in different ways. In some embodiments, for example, control unit 106 is used to determine one or more properties (e.g., size, hardness, and density) of occluded region 202 of blood vessel 200 and to make that information available to the user of ultrasound medical system 100. Control unit 106 can, for example, compare the energy parameters detected by ultrasound transducer 104 to the energy parameters emitted by ultrasound probe 110 to determine such characteristics of occluded region 202. In certain embodiments, control unit 106 includes a look-up table including: (1) data regarding initial vibrational energy emitted within a blood vessel; (2) data regarding vibrational energy detected by an ultrasound transducer disposed outside of the subject; and (3) data regarding one or more properties of a region of the blood vessel in which the initial vibrational energy was emitted. As discussed above, this data can be experimental data compiled by emitting vibrational energy in various different types of occlusions, detecting the vibrational energy using an ultrasound transducer disposed outside of the subject, and experimentally determining certain properties of the occlusions. In such embodiments, control unit 106 can determine one or more properties of occluded region 202 by matching the data regarding the property or properties of the occluded region with the data corresponding to both the energy detected by ultrasound transducer 104 and the energy initially emitted by ultrasound probe 110. In some embodiments, control unit 106 is connected to a display (e.g., a video and/or audio display) that can display the characteristics of occluded region 202 for the user. This information can be used to help the user effectively treat occluded region 202. The user can, for example, use this information to manually adjust power supply 112 and/or power supply 126 to deliver desired levels and patterns of electrical energy to ultrasound medical device 102 and/or ultrasound transducer 104. Alternatively or additionally, this information can be used to help the user select appropriate instruments to use to treat occluded region 202.

As an alternative to or in addition to determining one or more properties of occluded region 202, control unit 106 can be used to determine the state of occluded region 202 and to display the state of occluded region 202 to the user. Examples of possible states of occluded region 202 include acute, organized, chronic, etc. The state of occluded region 202 can be determined using techniques similar to those described above with regard to determining properties of occluded region 202.

As another example, while certain methods described above include determining the state of occluded region 202 based on the vibrational energy detected by ultrasound transducer 104, other techniques can alternatively or additionally be used to determine the state of occluded region 202. Examples of such techniques include imaging techniques and flow detection techniques (e.g., blood flow detection techniques).

As a farther example, while occluded region 202 of blood vessel 200 has been described as a thrombus, other types of occlusions can similarly be treated using methods described herein. Examples of other types of occlusions include occlusions resulting from plaque, stenoses, fibrous matter, calcific matter, and necrotic matter.

As an additional example, while embodiments above relate to treating an occluded region of a blood vessel, the techniques described herein can alternatively or additionally be used to treat other regions of a blood vessel. For example, the techniques can be used to treat atherosclerotic regions of blood vessels.

As another example, as an alternative to or in addition to treating blood vessels, other types of body vessels can be treated. Examples of other types of body vessels include lymphatic vessels, urinary tract vessels, and pleural vessels.

The systems and methods described herein can be used to treat any of various different medical conditions. Examples of medical conditions that can be treated include deep vein thrombosis (DVT), peripheral thrombosis (PT), peripheral artery disease, urolithiasis, chronic total occlusions, coronary bearing lesions, carotid occlusions, and neural occlusions.

Other embodiments are in the claims.

What is claimed is:

1. An ultrasound medical system, comprising:
   an ultrasound probe configured to be disposed within a body vessel of a subject and adapted to emit vibrational energy within the body vessel during use; and
   an ultrasound device configured to extracorporeally deliver vibrational energy to the body vessel during use, the vibrational energy delivered by the ultrasound device during use being capable of interacting with the vibrational energy emitted by the ultrasound probe during use to treat the body vessel;
   wherein the ultrasound device is configured to detect vibrational energy emitted by the ultrasound probe during use.

2. The medical system of claim 1, wherein the ultrasound device is adapted to extracorporeally deliver vibrational energy having a frequency substantially equal to a frequency of vibrational energy emitted from the ultrasound probe during use.

3. The medical system of claim 1, wherein the ultrasound device is adapted to extracorporeally deliver vibrational energy having a phase substantially equal to a phase of vibrational energy emitted from the ultrasound probe during use.

4. The medical system of claim 1, wherein the ultrasound device is configured to be disposed outside of the subject, adjacent the ultrasound probe.

5. The medical system of claim 1, wherein the ultrasound device comprises an ultrasound transducer.

6. The medical system of claim 1, wherein the ultrasound device comprises a high-intensity focused ultrasound transducer.

7. The medical system of claim 1, wherein the ultrasound device is adapted to be controlled based on the vibrational energy detected by the ultrasound device.

8. The medical system of claim 7, further comprising a control unit adapted to control the ultrasound device based on the vibrational energy detected by the ultrasound device.

9. The medical system of claim 1, wherein the ultrasound probe is adapted to be controlled based on vibrational energy detected by the ultrasound device.

10. The medical system of claim 9, further comprising a control unit adapted to control the ultrasound probe based on the vibrational energy detected by the ultrasound device.

11. A method, comprising:
    emitting a first vibrational energy within a region of a body vessel of a subject;
    detecting vibrational energy with an ultrasound device disposed outside of the subject; and
    extracorporeally delivering a second vibrational energy to the region of the body vessel, the first vibrational energy and the second vibrational energy being adapted to interact with one another to treat the body vessel.

12. The method of claim 11, wherein the first vibrational energy has a first frequency and the second vibrational energy has a second frequency substantially equal to the first frequency.

13. The method of claim 11, wherein the first vibrational energy has a first phase and the second vibrational energy has a second phase substantially equal to the first phase.

14. The method of claim 11, wherein emitting the first vibrational energy comprises vibrating an ultrasound probe disposed within the region of the body vessel.

15. The method of claim 11, wherein the second vibrational energy is extracorporeally delivered by an ultrasound device disposed outside of the subject.

16. The method of claim 11, further comprising extracorporeally delivering the second vibrational energy based on the vibrational energy detected by the ultrasound device.

17. The method of claim 11, further comprising emitting the first vibrational energy based on the vibrational energy detected by the ultrasound device.

18. A method, comprising:
    emitting a first vibrational energy within a body vessel of a subject using an ultrasound probe;
    detecting the vibrational energy with an ultrasound device disposed outside the subject; and
    extracorporeally delivering a second vibrational energy to the body vessel, the second vibrational energy being delivered based on the vibrational energy detected by the ultrasound device.

19. The method of claim 18, wherein the second vibrational energy is extracorporeally delivered based on a difference between the vibrational energy detected by the ultrasound device and the first vibrational energy.

20. The method of claim 18, wherein emitting the first vibrational energy comprises vibrating an ultrasound probe disposed within the body vessel.

21. The method of claim 20, further comprising vibrating the ultrasound probe based on the vibrational energy detected by the ultrasound device.

22. The method of claim 20, wherein the ultrasound probe is disposed within an occluded region of the body vessel.

23. The method of claim 22, further comprising determining a property of the occluded region of the vessel based on the vibrational energy detected by the ultrasound device.

24. The method of claim 23, wherein the property of the occluded region is determined based on a difference between the vibrational energy detected by the ultrasound device and the first vibrational energy.

25. The method of claim 23, wherein the property of the occluded region is determined based on one or more characteristics of the vibrational energy detected by the ultrasound device, the one or more characteristics being selected from the group consisting of frequency, amplitude, phase, duty cycle, and pulse repetition frequency.

26. The method of claim 18, wherein the second vibrational energy is extracorporeally delivered based on one or more characteristics of the vibrational energy detected by the ultrasound device, the one or more characteristics being selected from the group consisting of frequency, amplitude, phase, duty cycle, and pulse repetition frequency.

27. The method of claim 18, wherein the second vibrational energy is extracorporeally delivered by the ultrasound device.

28. The method of claim 18, wherein the first and second vibrational energies are adapted to interact with one another to treat the body vessel.

29. The method of claim 18, wherein the second vibrational energy has a frequency substantially equal to a frequency of the first vibrational energy.

30. The method of claim 18, wherein the second vibrational energy has a phase substantially equal to a phase of the first vibrational energy.

* * * * *